United States Patent
Ohtake

(10) Patent No.: US 8,623,914 B2
(45) Date of Patent: Jan. 7, 2014

(54) MEDICAL COMPOSITION

(75) Inventor: Nobuhiro Ohtake, Ibaraki (JP)

(73) Assignee: TSUMURA & Co., Tokyo (JP)

( * ) Notice: Subject to any disclaimer, the term of this patent is extended or adjusted under 35 U.S.C. 154(b) by 152 days.

(21) Appl. No.: 13/024,614

(22) Filed: Feb. 10, 2011

(65) Prior Publication Data

US 2012/0208878 A1 Aug. 16, 2012

(51) Int. Cl.
- *A01N 37/00* (2006.01)
- *A61K 31/21* (2006.01)
- *A01N 37/18* (2006.01)
- *A61K 31/16* (2006.01)
- *A61K 31/4965* (2006.01)

(52) U.S. Cl.
USPC .............. 514/506; 514/627; 514/255

(58) Field of Classification Search
USPC ........................ 514/506, 627, 255
See application file for complete search history.

(56) References Cited

U.S. PATENT DOCUMENTS 5,431,914 A * 7/1995 Adekunle et al. .............. 424/401
6,861,053 B1 * 3/2005 Lin et al. ...................... 424/93.1

OTHER PUBLICATIONS

Suzuki et al. (Neurogastroenterol Motil, 2009, 21, 688-696).*
Koo et al. (Eur J Neurosci, 2007, 1139-47).*
Ohya et al. (The Am J of Chinese Medicine, 31, 1, 129-135).*
Frissora et al. (Current Gastroenterology Reports, 2005, 7, 264-271).*
Sass (J Agric. Food Chem. vol. 25, 6, 1977).*

* cited by examiner

*Primary Examiner* — Sreeni Padmanabhan
*Assistant Examiner* — Uma Ramachandran
(74) *Attorney, Agent, or Firm* — Oblon, Spivak, McClelland, Maier & Neustadt, L.L.P.

(57) ABSTRACT

The object of the invention is to find the actions of the crude drugs contained in Daikenchuto or their components and the synergistic effect of the components with one another or with other pharmacologically active substances, and to provide new drugs or pharmaceutical compositions based on the findings. The invention is directed to intestinal peristaltic motility-enhancers comprising an effective amount of hydroxy-α-sanshool or a plant containing the same or an extract thereof; compositions comprising a combination of hydroxy-α-sanshool or a plant containing the same or an extract thereof and capsaicin or a plant containing the same or an extract thereof or bethanechol or a salt thereof; as well as a method for improving intestinal motility which comprises administering the composition to a patient.

15 Claims, 1 Drawing Sheet

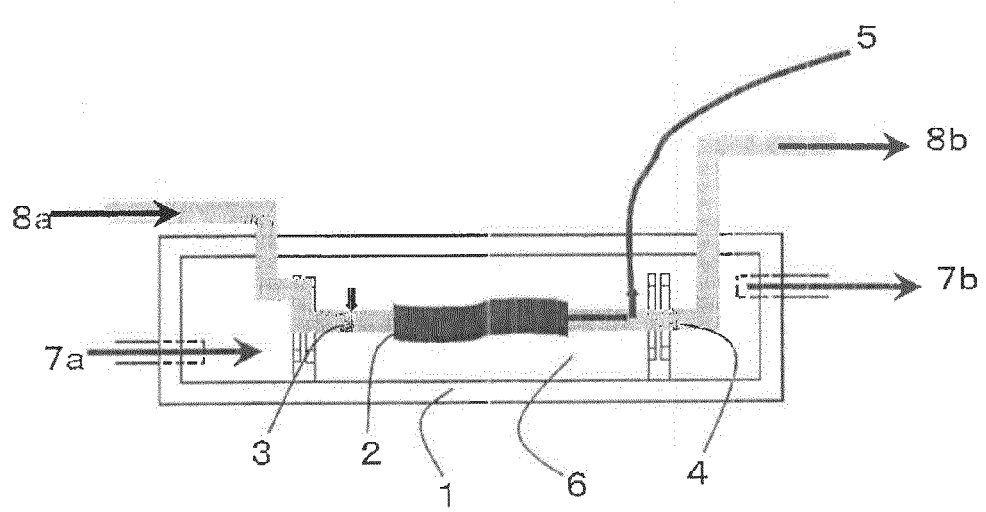

MEDICAL COMPOSITION

BACKGROUND OF THE INVENTION

1. Field of the Invention

The present invention relates to a medical composition. More particularly, it relates to a medical composition which is capable of enhancing intestinal motility synergistically.

2. Description of the Related Art

A kampo preparation is composed of a combination of crude drugs. A large number of crude drugs are known as ingredients used in kampo preparations, and their actions in a kampo preparation are considered to involve not only an additive effect of independent action of each crude drug, but also their synergistic effect.

A kampo preparation, Daikenchuto is a formulation prepared as a hot water extract from a mixture of crude drugs, Ginseng, Zanthoxylum Fruit (Shansho) and Processed Ginger (Kankyo) at a certain ratio with the addition of maltose. While this has been used in abdominal pain mainly caused by the chill, recent reports show that it is effective in the treatment of paralytic ileus after peritoneotomy. Further, even in intestinal obstruction by adhesion, it is also reported that the combined use of Daikenchuto in the conservative therapy (drainage or evacuation by insertion of an ileus tube) improves the symptoms such as abdominal distension or nausea, reduces the necessity of surgical operation, and prevents recurrence of the intestinal obstruction.

The present inventor has noticed the prokinetic effect of Daikenchuto on the intestinal peristaltic motility and tried to identify the crude drugs that act effectively among the ingredients of Daikenchuto. As a result, the inventor has found that Zanthoxylum Fruit and Processed Ginger have such an effect but neither in itself exhibits such a prokinetic effect on the intestinal peristaltic motility as in Daikenchuto at the concentration contained in Daikenchuto.

It is important to find respective actions of the crude drugs contained in Daikenchuto or their components and the synergistic effect among the components, since finding an unknown synergistic effect among the crude drugs or their components as mentioned above clearly leads to a novel approach for treating diseases.

SUMMARY OF THE INVENTION

Thus, the present invention aims to find out the actions of the crude drugs contained in Daikenchuto or their components and the synergistic effect of the components with one another or with other pharmacologically active substances, and to provide new drugs or pharmaceutical compositions based on the findings.

The inventor has focused on the prokinetic effect of Daikenchuto on the intestinal peristaltic motility and worked to identify the components of crude drugs involved in this effect. As a result, the inventor has found that 6-shogaol and 6-gingerol, the major components of Processed Ginger, and hydroxy-α-sanshool, the major component of Zanthoxylum Fruit, separately has the action. In addition, it was found that, though the prokinetic effect of hydroxy-α-sanshool on the intestinal peristaltic motility is relatively small, a combination of hydroxy-α-sanshool with 6-shogaol or 6-gingerol synergistically enhances the effect. Further investigations into whether the intestinal peristaltic motility is promoted by a combination of hydroxy-α-sanshool and other pharmacologically active substances with the action have found the synergistically prokinetic effect on the intestinal peristaltic motility for some of the substances. Thus, the invention was completed.

Specifically, the present invention comprises the following content.

1. An intestinal peristaltic motility-enhancer comprising an effective amount of hydroxy-α-sanshool.
2. A method of enhancing the action of an intestinal peristaltic motility-promoter in a subject in need thereof which comprises administering to the subject an effective amount of hydroxy-α-sanshool.
3. A composition comprising an intestinal motility-enhancing synergistic combination of hydroxy-α-sanshool and capsaicin.
4. A composition comprising an intestinal motility-enhancing synergistic combination of a plant containing hydroxy-α-sanshool or an extract thereof and a plant containing capsaicin or an extract thereof.
5. A method of improving intestinal motility in a subject in need thereof which comprises administering to the subject a composition comprising an intestinal motility-enhancing synergistic combination of hydroxy-α-sanshool and capsaicin.
6. A method of improving intestinal motility in a subject in need thereof which comprises administering to the subject a composition comprising an intestinal motility-enhancing synergistic combination of a plant containing hydroxy-α-sanshool or an extract thereof and a plant containing capsaicin or an extract thereof.
7. A method of treating an intestinal motility disorder in a subject in need thereof which comprises administering to the subject a composition comprising an intestinal motility-enhancing synergistic combination of hydroxy-α-sanshool and capsaicin.
8. A method of treating an intestinal motility disorder in a subject in need thereof which comprises administering to the subject a composition comprising an intestinal motility-enhancing synergistic combination of a plant containing hydroxy-α-sanshool or an extract thereof and a plant containing capsaicin or an extract thereof.
9. A composition comprising an intestinal motility-enhancing synergistic combination of hydroxy-α-sanshool and bethanechol.
10. A method of improving intestinal motility in a subject in need thereof which comprises administering to the subject a composition comprising an intestinal motility-enhancing synergistic combination of hydroxy-α-sanshool and bethanechol.
11. A method of treating an intestinal motility disorder in a subject in need thereof which comprises administering to the subject a composition comprising an intestinal motility-enhancing synergistic combination of hydroxy-α-sanshool and bethanechol.
12. A method of enhancing TRPV1 agonistic activity in a subject in need thereof which comprises administering to the subject an effective amount of hydroxy-α-sanshool.

The intestinal peristaltic motility-enhancer of the present invention can, in combination with other pharmacologically active substances having the prokinetic effect on intestinal peristaltic motility, synergistically enhance the effect of the substances, and is useful in the treatment of paralytic ileus, gastrointestinal hypofunction observed in chronic gastritis or after operation or delivery, chronic constipation, and constipated irritable bowel syndrome.

The composition of the present invention in which hydroxy-α-sanshool is combined with capsaicin or bethanechol is capable of enhancing synergistically intestinal peristaltic motility, and is useful for improving intestinal motility or for treating an intestinal motility disorder.

BRIEF DESCRIPTION OF THE DRAWINGS

FIG. 1 shows a schematic diagram of an apparatus used in measurement of the intestinal peristaltic motility.

DETAILED DESCRIPTION

The term "improving intestinal motility or treating an intestinal motility disorder" as used herein, means increasing the frequency and pressure amplitude in the peristaltic motility of the digestive tract, mainly of large intestine or small intestine. More specifically, increase in the constriction frequency in the small intestinal peristaltic motility promotes agitation of intestinal content and transportation toward the cecum. Increase in the luminal pressure with the large intestinal peristaltic motility leads to the stimulation of excretion of the content piling up in the large intestine (feces) toward the anus. Thus, the prokinetic effect on intestinal peristaltic motility means therapy or improvement of paralytic ileus after surgical operation, gastrointestinal hypofunction observed in chronic gastritis or after operation or delivery, constipated condition in irritable bowel syndrome, chronic constipation and the like.

Hydroxy-α-sanshool (hereinafter abbreviated as "HAS") used in the present invention is a component contained in Zanthoxyli plants including *Zanthoxylum piperitum*, *Zanthoxylum bungeanum*, and *Zanthoxylum schinifolium*, and is represented by the following formula (I):

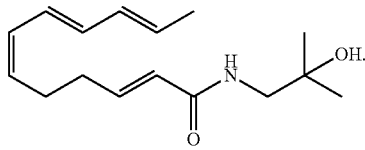 [SMILES: C/C=C/C=C/C=C\CC/C=C/C(=O)NCC(C)(C)O]

This compound has already been known, and can be obtained according to a conventional way, for example, by extraction of the dry pericarp of the Zanthoxyli plant with an oil-soluble solvent such as organic solvent under heating or by immersion and purification, extraction with hot water and purification, and supercritical fluid extraction and purification, or by purification of the juice squeezed from the raw pericarp, or by chemical synthesis.

In order to prepare the intestinal peristaltic motility-enhancer using HAS, HAS may be mixed with pharmaceutically acceptable carrier(s) to form a pharmaceutical preparation according to a conventional way. The formulation of this preparation includes liquid, powder, or capsules, tablets or granules prepared from the powder.

The intestinal peristaltic motility-enhancer may be combined with other drug(s) promoting intestinal peristaltic motility including a TRPV1 agonist such as 6-shogaol, 6-gingerol, capsaicin, or a cholinergic agent such as bethanechol or salts thereof. The amount of HAS to be administered as this formulation may be 1 mg to 100 mg, preferably 1.5 mg to 15 mg, per day for an adult, which may be taken once in a single dose or several times in divided doses.

The present invention also provides a composition in which HAS is combined with another drug promoting intestinal peristaltic motility.

A specific example of the compositions includes a composition comprising a combination of HAS and capsaicin (hereinafter abbreviated as "CAP"), by which intestinal motility can be enhanced synergistically.

CAP used in the composition is a representative TRPV1 agonist, which binds to a TRPV1 receptor to promote the movement of the digestive tract and induce excretion of feces, and desensitizes the sensory nerve to suppress transduction of painful irritation.

CAP is a known compound contained in Capsici plants such as *Capsicum annuum* L, *Capsicum chinense*, and *Capsicum frutescens* L, which can be obtained according to a conventional way by extraction of the pericarp of these plants with an oil-soluble solvent such as organic solvent under heating or by immersion and purification, extraction with hot water and purification, or supercritical fluid extraction and purification, or by chemical synthesis.

The composition comprising HAS and CAP may be prepared according to a conventional way by mixing them with pharmaceutically acceptable carrier(s) to form a pharmaceutical preparation. The formulation of this preparation includes liquid, powder, or capsules, tablets or granules prepared from the powder.

The combined ratio of HAS and CAP in the composition is in the range of 300:1 to 3:1, preferably 100:1 to 10:1 (molar ratio). The amount of the composition to be administered may be 1 to 100 mg, preferably 3 to 20 mg, per day for an adult, which may be taken once in a single dose or several times in divided doses.

HAS and CAP each is a component contained in crude drugs, and may be formed into a composition in an unpurified state. Thus, it is possible to combine a plant containing HAS (*Zanthoxylum piperitum*, *Zanthoxylum bungeanum*, *Zanthoxylum schinifolium* or the like) or its extract with a plant containing CAP (*Capsicum annuum* L, *Capsicum chinense*, *Capsicum frutescens* L or the like) or its extract to prepare the composition of the present invention. In this composition, the ratio and amount of HAS and CAP contained in the plants or their extract are preferably in the range as mentioned above.

Another specific example of the compositions includes a composition comprising a combination of HAS and bethanechol (hereinafter abbreviated as "Beth") or salt thereof, by which intestinal motility can be enhanced synergistically.

Beth used in the composition is one of cholinergic agents belonging to choline esters, which binds to a muscarine receptor to exhibit a parasympatheticomimetic action. This is considered to have a strong action on the digestive tract or the smooth muscle of bladder and a weak action on the circulatory system, and has been utilized as an urination promoter.

The composition comprising HAS and Beth may also be prepared according to a conventional way by mixing them with pharmaceutically acceptable carrier(s) to form a pharmaceutical preparation. The formulation of the preparation includes powder, or capsules, tablets or granules prepared from the powder.

The combined ratio of HAS and Beth in the composition is in the range of 6:1 to 1:2, preferably 3:1 to 1:1 (molar ratio). The amount of the composition to be administered may be 1 to 100 mg, preferably 4 to 30 mg, per day for an adult, which may be taken once in a single dose or several times in divided doses.

As mentioned above, the plant containing HAS or its extract may be utilized in the composition of the present invention without purification. As Beth, a proper salt of bethanechol such as hydrochloride may be preferably utilized.

The intestinal peristaltic motility-enhancer of the present invention may be administered to a subject in combination with other pharmacologically active substances promoting intestinal peristaltic motility as mentioned above in order to improve the intestinal motility or treat the intestinal motility disorder. The action of HAS is considered to enhance the TRPV1 agonist activity in a subject to whom HAS is administered, and thereby synergistically enhance the action of CAP or Beth.

EXAMPLES

The present invention will be explained more in detail by the following Tests, which are not intended to limit the invention.

Test 1
Investigation of the Action of Each Crude Drug Component Contained in Daikenchuto on the Large Intestinal Peristaltic Motility:

Rats were used as experimental animals. According to the following way, the components contained in Daikenchuto, i.e., HAS, 6-shogaol (hereinafter abbreviated as "6-S") and 6-gingerol (hereinafter abbreviated as "6-G"), were tested for the action on the peristaltic motility. Table 1 shows the results.

(Breeding of Rats)

Male SD rats (provided by Japan Charles River Co.; SPF animals) were obtained at 6 weeks of age (body weight: 190-220 g) and the test was started at 7-9 weeks of age (body weight: 220-280 g at acquisition and using). Breeding was conducted at a temperature of 20-26° C. and a humidity of 35-75%, in aeration frequency of 15-25/hour in a cage under lighting for 12 hours (7 o'clock to 19 o'clock) per day, wherein 4 rats were placed in a cage. For feeding, solid feed MF (Oriental Yeast Co., Ltd.) was used, and the rats were able to freely drink ordinary tap water (Amimachi, Ibaraki Pref).

(Method of Measurement of the Intestinal Peristaltic Motility)

Normal rats which fasted overnight with free access to water were decapitated for mercy killing. Immediately, the intestine was removed and cut into 3-4 cm pieces, which were used as test samples. The removed test samples were immersed in an organ bath (perfusion rate: 3.5 mL/min) filled with a Krebs solution warmed at 32-33° C. and saturated with 95% $O_2$/5% $CO_2$ gas mixture. In the test samples, as shown in FIG. 1, tubes were connected to both ends of the samples (the mouth side and the anal side). From the mouth side, physiological saline was injected at a certain rate (0.15 mL/min), and the frequency and amplitude of the pressure change in the lumen caused by the intestinal peristaltic motility were measured by means of a microchip pressure transducer (SPR-524, Millar Instruments Co.). After confirmation of the stabilized peristaltic motility in the test samples (intestinal tract), a test drug was added to the organ bath. Before and after the addition, the change of peristaltic motility for 10 minutes was determined by using recorded wave profile for the mean peak pressure amplitude (mean-PPA), the area under curve (AUC) of the peak and the peak frequency (PF) in the transducer. The resulting recorded wave profile was converted into numerical terms as the amplitude or frequency of the peristaltic motility by an analysis software. The value before the addition of the test drug was regarded as 100% for comparison and evaluation.

(Result)

TABLE 1

| Test Drug | Concentration (μM) | Mean-PPA* (%) | AUC** (%) | PF*** (%) |
|---|---|---|---|---|
| HAS | 3 | 119.5 | 121.5 | 98.3 |
|  | 10 | 478.2 | 227.9 | 52.5 |
| 6-S | 1 | 202.6 | 133.3 | 102.6 |
|  | 10 | 94.6 | 73.4 | 120.8 |
| 6-G | 1 | 141.1 | 120.5 | 115.0 |
|  | 10 | 304.2 | 188.2 | 76.9 |

*MEAN OF PEAK PRESSURE AMPLITUDE
**AREA UNDER CURVE PEAK
***PEAK FREQUENCY

The results showed that HAS has no influence on the peristaltic motility at 3 μM, but it causes a very strong prokinetic effect at 10 μM. On the other hand, in 6-S, the peristaltic motility was promoted weakly at 1 μM, but the prokinetic effect disappeared at 10 μM. 6-G showed a weak prokinetic effect on peristaltic motility at 1 μM and a significant prokinetic effect at 10 μM.

Test 2
Investigation of the Action of Crude Drug Components on the Peristaltic Motility (1):

On the basis of the prokinetic effect of HAS, 6-S and 6-G on peristaltic motility in Test 1, the change of the prokinetic effect in a combination of these compounds was investigated in the same manner as in Test 1. Table 2 shows the results.

TABLE 2

| Test Drug | Concentration (μM) | Mean-PPA* (%) | AUC** (%) | PF*** (%) |
|---|---|---|---|---|
| HAS | (3) | 101.2 | 99.0 | 93.0 |
| 6-S | (1) | 202.6 | 133.3 | 115.0 |
| 6-S + HAS | (1 + 3) | 289.4 | 201.4 | 97.9 |
| 6-G | (3) | 235.8 | 174.9 | 102.9 |
| 6-G + HAS | (3 + 3) | 510.1 | 357.1 | 98.2 |

*MEAN OF PEAK PRESSURE AMPLITUDE
**AREA UNDER CURVE PEAK
*** PEAK FREQUENCY

The results showed that the potent enhancement of the prokinetic effect on peristaltic motility is obtained by combining 6-S or 6-G with HAS at a dose which is too low to exert the effect when used alone. Thus, the plant containing HAS or its extract is capable of enhancing synergistically the intestinal peristaltic motility induced by the plants containing 6-S or 6-G, the Zingiberaceae plant (*Zingiber officinale* ROSCOE, *Zingiber offcinale* var. *Rubra* or the like) or its extract.

Test 3
Investigation of the Action of Crude Drug Components on the Peristaltic Motility (2):

The respective prokinetic effect of HAS and CAP on peristaltic motility and change of the effect in a combination of these compounds were investigated in the same manner as in Test 1. Table 3 shows the results.

TABLE 3

| Test Drug | Concentration (μM) | Mean-PPA* (%) | AUC** (%) | PF*** (%) |
|---|---|---|---|---|
| HAS | (3) | 105.7 | 110.2 | 98.7 |
| CAP | (0.03) | 143.7 | 147.1 | 108.1 |
| CAP + HAS | (0.03 + 3) | 531.7 | 317.1 | 114.2 |

*MEAN OF PEAK PRESSURE AMPLITUDE
**AREA UNDER CURVE PEAK
***PEAK FREQUENCY

As shown in table 3, HAS enhanced the increases in PPA and AUC induced by CAP by about 9.8 times and 4.6 times, respectively.

Test 4

Investigation of the Action of Crude Drug Components on the Peristaltic Motility (3):

The respective prokinetic effect of HAS and bethanechol chloride (Beth) on peristaltic motility and change of the effect in a combination of these compounds were investigated in the same manner as in Test 1. Table 4 shows the results.

TABLE 4

| Test Drug | Concentration (μM) | Mean-PPA* (%) | AUC** (%) | PF*** (%) |
| --- | --- | --- | --- | --- |
| HAS | (3) | 105.2 | 130.6 | 84.6 |
| Beth | (1) | 98.9 | 87.6 | 153.8 |
| Beth + HAS | (1 + 3) | 107.8 | 140.3 | 330.8 |

*MEAN OF PEAK PRESSURE AMPLITUDE
**AREA UNDER CURVE PEAK
***PEAK FREQUENCY

As shown in table 4, HAS enhanced the increase in PF induced by Beth twice or more.

The intestinal peristaltic motility-enhancer of the present invention, when used in combination with other pharmacologically active substances having the prokinetic effect on intestinal peristaltic motility, is capable of enhancing synergistically the effect of the substances.

Further, the composition of the present invention comprising a combination of hydroxy-α-sanshool and capsaicin or bethanechol is capable of enhancing synergistically the intestinal peristaltic motility.

Thus, the present invention can effectively be utilized in improvement of the intestinal motility or in development of new drugs or pharmaceutical compositions useful in the treatment of intestinal motility disorder.

What is claimed is:

1. A method of enhancing an action of an intestinal peristaltic motility promoter in a subject in need thereof which comprises administering to the subject an effective amount of a combination of hydroxy-α-sanshool and capsaicin; or hydroxyl-α-sanshool and bethanechol wherein the administering of hydroxy-α-sanshool is in an amount of 1 mg to 100 mg per day, wherein the hydroxy-α-sanshool and the capsaicin are administered in a ratio of 300:1 to 3:1, wherein the hydroxy-α-sanshool and the bethanechol are administered in a ratio of 6:1 to 1:2.

2. A method of improving intestinal motility in a subject in need thereof, the method comprising administering to the subject an effective amount of a combination of hydroxy-α-sanshool and capsaicin; or hydroxyl-α-sanshool and bethanechol wherein the administering of hydroxy-α-sanshool is in an amount of 1 mg to 100 mg per day, wherein the hydroxy-α-sanshool and the capsaicin are administered in a ratio of 300:1 to 3:1, wherein the hydroxy-α-sanshool and the bethanechol are administered in a ratio of 6:1 to 1:2.

3. A method of treating an intestinal motility disorder in a subject in need thereof, the method comprising administering to the subject an effective amount of a combination of hydroxy-α-sanshool and capsaicin; or hydroxyl-α-sanshool and bethanechol wherein the administering of hydroxy-α-sanshool is in an amount of 1 mg to 100 mg per day, wherein the hydroxy-α-sanshool and the capsaicin are administered in a ratio of 300:1 to 3:1, wherein the hydroxy-α-sanshool and the bethanechol are administered in a ratio of 6:1 to 1:2.

4. The method of claim 1, wherein the hydroxy-α-sanshool and the capsaicin are administered and the hydroxy-α-sanshool is comprised in an extract or portion of a Zanthoxyli plant and the capsaicin is comprised in an extract or portion of a Capsici plant.

5. The method of claim 2, wherein the hydroxy-α-sanshool and the capsaicin are administered and the hydroxy-α-sanshool is comprised in an extract or portion of a Zanthoxyli plant and the capsaicin is comprised in an extract or portion of a Capsici plant.

6. The method of claim 3, wherein the hydroxy-α-sanshool and the capsaicin are administered and the hydroxy-α-sanshool is comprised in an extract or portion of a Zanthoxyli plant and the capsaicin is comprised in an extract or portion of a Capsici plant.

7. The method of claim 1, wherein the hydroxy-α-sanshool and the bethanecol are administered and the hydroxy-α-sanshool is comprised in an extract or portion of a Zanthoxyli plant.

8. The method of claim 2, wherein the hydroxy-α-sanshool and the bethanecol are administered and the hydroxy-α-sanshool is comprised in an extract or portion of a Zanthoxyli plant.

9. The method of claim 3, wherein the hydroxy-α-sanshool and the bethanecol are administered and the hydroxy-α-sanshool is comprised in an extract or portion of a Zanthoxyli plant.

10. The method of claim 1, wherein the hydroxy-α-sanshool and the capsaicin are administered in purified form, optionally in a composition that comprises a pharmaceutically acceptable carrier.

11. The method of claim 2, wherein the hydroxy-α-sanshool and the capsaicin are administered in purified form, optionally in a composition that comprises a pharmaceutically acceptable carrier.

12. The method of claim 3, wherein the hydroxy-α-sanshool and the capsaicin are administered in purified form, optionally in a composition that comprises a pharmaceutically acceptable carrier.

13. The method of claim 1, wherein the hydroxy-α-sanshool and the bethanecol are administered in purified form, optionally in a composition that comprises a pharmaceutically acceptable carrier.

14. The method of claim 2, wherein the hydroxy-α-sanshool and the bethanecol are administered in purified form, optionally in a composition that comprises a pharmaceutically acceptable carrier.

15. The method of claim 3, wherein the hydroxy-α-sanshool and the bethanecol are administered in purified form, optionally in a composition that comprises a pharmaceutically acceptable carrier.

* * * * *